United States Patent [19]

Schwan et al.

[11] 4,105,850
[45] Aug. 8, 1978

[54] 1-AMINO-3-(4-CHLOROPHENYL)-2-IMIDAZOLIDINONE

[75] Inventors: Thomas J. Schwan; Ralph L. White, Jr., both of Norwich, N.Y.

[73] Assignee: Morton-Norwich Products, Inc., Norwich, N.Y.

[21] Appl. No.: 796,611

[22] Filed: May 13, 1977

[51] Int. Cl.$^2$ .............................. C07D 233/46
[52] U.S. Cl. .................. 548/319; 424/273 R
[58] Field of Search ......................... 548/319

[56] References Cited

U.S. PATENT DOCUMENTS

| 2,746,960 | 5/1956 | Gever et al. | 548/319 |
| 2,776,979 | 1/1957 | Michels | 548/319 |
| 2,920,074 | 1/1960 | Michels | 548/319 |
| 3,115,499 | 12/1963 | Michels | 548/319 |
| 3,905,996 | 9/1975 | Perronnet et al. | 548/319 |

OTHER PUBLICATIONS

Michels et al., J. Amer. Chem. Soc. 1956, vol. 78, pp. 5349–5351.
Palazzo et al., Chem. Abst. 1971, vol. 75, No. 76749v.

*Primary Examiner*—Natalie Trousof
*Attorney, Agent, or Firm*—Anthony J. Franze

[57] ABSTRACT

A compound 1-amino-3-(4-chlorophenyl)-2-imidazolidinone possesses pharmacological activity as an antidepressant.

1 Claim, No Drawings

1-AMINO-3-(4-CHLOROPHENYL)-2-IMIDAZOLIDINONE

This invention relates to the chemical compound 1-amino-3-(4-chlorophenyl)-2-imidazoidinone sulfate.

This compound possesses pharmacological activity effecting the central nervous system. When administered perorally to animals it exhibits antidepressant action. Its antidepressant property is evidenced in the control of tetrabenazine-induced ptosis in mice. An oral dose of 50 mg/kg of this compound to mice intraperitoneally receiving 35 mg/kg of tetrabenazine counteracts the ptosis producing property of tetrabenazine.

In order that this invention be readily available to and understood by those skilled in the art, the following example is supplied:

A. 1-(4-Chlorophenyl)-3-nitroso-2-imidazolidinone

In a solution of glacial acetic acid (2750 ml) and water (250 ml) was dissolved 150 g (0.75 mol) of 1-(4-chlorophenyl)-2-imidazolidinone with heating. The solution was cooled to room temperature, and sodium nitrite (70 g, 1.0 mol) in water (200 ml) was added dropwise over 1 hr. The mixture was stirred for another 6 hrs, diluted with water (1.5 l) and the product (137 g, 81%) was collected m.p. 154°–156°.

B. 1-Amino-3-(4-chlorophenyl)-2-imidazolidinone

To a solution of dioxane (1 l.) and 4N $H_2SO_4$ (1 l.) was added 113 g (0.50 mol) of A. The creamy yellow mixture was cooled and maintained at about 10° and zinc powder (65 g) was added in portions over 1.5 hr. The mixture was stirred another 24 hrs and then filtered. The collected solid was set aside. The filtrate was diluted with water to yield more solid. This product was recrystallized from water (10 l.) to yield B (22 g) after filtration to remove recovered A. The solid which had been set aside was recrystallized from 50% aq. ethanol (v/v, 8 l.) to yield another 13 g of the product, a yield of 27%.

An analytical sample, m.p. 241°–245°, was obtained by recrystallization from ethanol.

Anal. Calc'd. for $C_9H_{10}ClN_3O.\frac{1}{2} H_2SO_4$: C, 41.73; H, 4.25; N, 16.12. Found: C, 41.37; H, 4.22; N, 16.26.

What is claimed is:

1. The compound 1-Amino-3-(4-chlorophenyl)-2-imidazolidinone.